United States Patent [19]

Van Eden et al.

[11] Patent Number: 5,154,923
[45] Date of Patent: Oct. 13, 1992

[54] POLYPEPTIDES AND DERIVATIVES THEREOF AS WELL AS THEIR USE IN PHARMACEUTICAL AND DIAGNOSTIC COMPOSITIONS

[75] Inventors: Willem Van Eden, Bilthoven; Johannes D. A. Van Embden; Ruurd Van der Zee, both of Utrecht, all of Netherlands; Irun R. Cohen, Rehovot, Israel

[73] Assignees: De Staat Der Nederlanden Vertegenwoordigd Door de Minister Van Welzijn, Volksgezondheid En Cultuur; Rijksuniversiteit Te Utrecht, both of Netherlands; Yeda Research and Development Co., Ltd., Israel

[21] Appl. No.: 288,080

[22] Filed: Dec. 21, 1988

[30] Foreign Application Priority Data

Dec. 22, 1987 [NL] Netherlands ............ 8703107

[51] Int. Cl.$^5$ ............ A61K 39/385; A61K 39/04; A61K 37/12; C07K 7/06
[52] U.S. Cl. ............ 424/88; 424/89; 424/92; 530/324; 530/325; 530/326; 530/327; 530/328; 530/330; 530/345; 530/405; 514/12; 514/13; 514/14; 514/15; 514/21; 435/188; 435/207
[58] Field of Search ............ 530/326, 328, 330, 324, 530/325, 327, 405, 345; 514/13, 15, 18, 12, 21, 14, 15; 424/92, 89, 88; 930/200, 220, 290; 435/188, 207

[56] References Cited

U.S. PATENT DOCUMENTS

| | | | |
|---|---|---|---|
| 4,689,397 | 8/1987 | Shinnick et al. | 530/327 |
| 4,772,685 | 9/1988 | Schmidt et al. | 530/326 |
| 4,777,239 | 10/1988 | Schoolnik et al. | 530/326 |
| 4,857,634 | 8/1989 | Minor et al. | 530/324 |

OTHER PUBLICATIONS

Rudinger in J. A. Parsons ed *Peptide Horone* Univ. Park Press Baltimore Jun. 1976 pp. 1–7.
Shinnick (1987) J. Bacteriol 169(3):1080–1088.
Shinnick et al. (1987) Infecet. Immunity 55(8):1932–1935.
Brief Definitive Report–A Recombinant 64 Kioldalton Protein of *Mycobacterium bovis* Bacillus Calmetter Cuerin Specifically Stimulates Human T4 Clones Reactive to Mycobacterial Antigens by Emmrich et al. pp. 1025–1029.
Evidence for an HLA–DRA4–Associated Immune—Response Gene For Mycobacterium Tuberculosis-A Clue to the Pathogenesis of Rheumatoid Arthritis? By Tome H. M. Ottenhoff et al. pp. 310–313—The Lancet Aug. 9, 1986
Dissection of *Mycobacterium tuberculosis* antigens using recombinant DNA. By Richard A. Young et al., Proc. Natl. Acad. Sci USA vol. 82 pp. 2583–2587 May, 1989—Biochemistry.
Vol. 105, 1986 p. 525 Chem Abstracts, Abst. #151096y. Cloning of *Mycobacterium bovis* BCG DNA and Expression of Antigens in *Escherichia coli* Jelle E. R. Thole et al. Received Jun. 17, 1985 Accepted Sep. 3, 1985 pp. 800–806 vol. 50 No. 3.
Characterization, sequence Determination and Immunogenicity of a 64-Kilodalton Protein of *Mycobacterium bovis* BCG Expressed in *Escherichia coli* K–12 by Thole et al. vol. 55 No. 6 received Nov. 21, 1986 accepted Feb. 23, 1987, pp. 1466–1475.
The Etiologic Agents of Leprosy and Tuberculosis Share an Immunoreactive Protein Antigen with the Vaccine Strain *Mycobacterium bovis* BCG by Thole et al. Infection and Immunity Aug. 1987, pp. 1932–1935.
Chemical Abstracts vol. 103 (1985) Abstract No. 69497e, M. J. Darsley et al.

*Primary Examiner*—Christine M. Nucker
*Assistant Examiner*—Kay Kim
*Attorney, Agent, or Firm*—Brumbaugh, Graves, Donohue & Raymond

[57] ABSTRACT

A polypeptide having amino acid sequence 172–192 of a *Mycobacterium bovis* BCG 64 kD polypeptide, said sequence having the formula

```
172         180         188   192
VITVEESNTFGLQLELTEGMR
``` as well as polypeptides derived therefrom, in the amino acid sequence of which sequence 172–179 and/or sequence 189–192 is (are) entirely or partially absent, were found to be useful as immunogens inducing resistance to auto-immune arthritis and similar auto-immune diseases.

The invention relates to these polypeptides, to polypeptides showing sequential homology with these polypeptides, and to derivatives and multimers thereof. Also, microorganisms expressing the polypeptides either as such or as part of a fusion protein or as a multimer form part of the invention.

Finally, the invention relates to pharmaceutical compositions, diagnostic compositions and test kits comprising a compound according to the invention.

13 Claims, No Drawings

POLYPEPTIDES AND DERIVATIVES THEREOF AS WELL AS THEIR USE IN PHARMACEUTICAL AND DIAGNOSTIC COMPOSITIONS

The present invention relates to polypeptides and derivatives thereof suitable for alleviation, treatment and diagnosis of auto-immune diseases, especially arthritic conditions. Further, the invention relates to pharmaceutical and diagnostic compositions comprising these compounds, and to test kits for performing immunological tests.

BACKGROUND OF THE INVENTION

Millions of persons are afflicted with chronic forms of arthritis which are thought to involve auto-immunity to constituents of the joints or connecting tissues of the body. These conditions include rheumatoid arthritis, ankylosing spondylitis, Reiter's syndrome and other forms of reactive arthritis. The etiology of these diseases is not known, but previous infection with various microbes seems to act as an inciting circumstance in genetically susceptible individuals. For example, patients with rheumatoid arthritis may show unusual reactivity to mycobacterial antigens, and immunisation with the BCG strain of mycobacteria was found to lead to arthritis in 15 of 150 individuals. Ankylosing spondylitis has been associated with infection by Klebsiella or Yersinia species of bacteria and other cases of arthritis by Salmonella, Shigella, etc. There is no evidence of active infection of joints by these microbes in the vast majority of cases and it has been postulated that microbial infection may trigger an apparent auto-immune response of the individual against his own antigens present in the joints. Adjuvant arthritis (AA) is an experimental model of arthritis inducible by immunizing susceptible strains of rats to Mycobacteria. The disease which develops about twelve days after immunisation has many of the features of rheumatoid arthritis and AA has been considered to be a model of rheumatoid arthritis.

PRIOR ART

EP-A-0 181 364 discloses aqueous acetone soluble and insoluble fractions of certain mycobacteria, such as Mycobacterium H-37, *M. kansasii* and *M. vaccae*. The soluble fraction of Myc. H-37 was found to provoke an immune response leading to resistance to adjuvant arthritis. The insoluble fraction seemed to be responsible for the induction of adjuvant arthritis. *Mycobacterium vaccae* was shown to be substantially free of adjuvant arthritis inducing components. Further, EP-A 0 181 364 describes certain lines and clones of T-lymphocytes selected for their reactivity to mycobacteria. These lines and clones can be used for producing arthritis upon inoculation into irradiated rats. One of the lines, designated as A2 was found to induce arthritis upon intraveneous injection into irradiated rats. The same line, A2, is effective in vaccinating unirradiated rats against subsequent auto-immune arthritis induced by active immunization to mycobacteria. Cell line A2 has been cloned. There were obtained two distinct clones, designated as A2b and A2c, respectively. A2b causes arthritis but does not vaccinate against it, clone A2c does not cause arthritis but vaccinates against it. In addition to preventing arthritis, clone A2c can be used to treat AA. Moreover, clones A2b and A2c can be used to identify antigens associated with arthritogenicity or with suppression of arthritogenicity. Both clones respond to whole mycobacteria as well as to cartilage proteoglycan protein.

It is stated in European patent application 87 201691.0 (Publication Nr. 0 262 710) filed Sep. 7, 1987 that a polypeptide having a molecular mass of about 64 kD, the preparation of which is described in Infection and Immunity 1985, pages 800–806, is useful as an immunogen inducing resistance against auto-immune arthritis and similar auto-immune diseases.

In the abovementioned article the peptide in question is called antigen A and this designation will be used here as well. According to the article antigen A was obtained by constructing a gene bank of *Mycobacterium bovis* BCG DNA in *Escherichia coli* by cloning Sau3A-cleaved mycobacterium DNA fragments into the lambda vector EMBL3. The expression of mycobacterial antigens was analyzed by Western Blotting with hyperimmune rabbit sera. The article states that among 770 clones tested, several were found that produced various mycobacterial antigens in low amounts, with concentrations generally close to the detection limit. One particular clone was chosen for further investigation. This clone produced a 64 kD antigen. By placing the lambda promotor $P_L$ in front of the structural gene of this antigen, an overproducing *E. coli* strain was obtained. The article shows that antigens cross-reacting with the 64 kD protein are present in a wide variety of mycobacteria and also in so-called purified protein derivatives which are routinely used for skin tests. Finally, it is stated in the article that preliminary experiments indicate the presence of antibodies against the 64 kD antigen in sera from tuberculosis patients.

European patent application 0 262 710 also describes the amino acid sequence of antigen A:

| | |
|---|---|
| 1 | fMAKTIAYDEE ARRGLERGLN ALADAVKVTL GPKGRNVVLE KKWGAPTITN DGVSIAKEIE |
| 61 | LEDPYEKIGA ELVKEVAKKT DDVAGDGTTT ATVLAQALVR EGLRNVAAGA NPLGLKRGIE |
| 121 | KAVEKVTETL LKGAKEVETK EQIAATAAIS AGDQSIGDLI AEAMDKVGNE GVITVEESNT |
| 181 | FGLQLELTEG MRFDKGYISG YFVTDPERQE AVLEDPYILL VSSKVSTVKD LLPLLEKVIG |
| 241 | AGKPLLIIAE DVEGEALSTL VVNKIRGTFK SVAVKAPGFG DRRKAMLQDM AILTGGQVIS |
| 301 | EEVGLTLENA DLSLLGKARK VVVTKDETTI VEGAGDTDAI AGRVAQIRQE IENSDSDYDR |
| 361 | EKLQERLAKL AGGVAVIKAG AATEVELKER KHRIEDAVRN AKAAVEEGIV AGGGVTLLQA |
| 421 | APTLDELKLE GDEATGANIV KVALEAPLKQ IAFNSGLEPG VVAEKVRNLP AGHGLNAQTG |
| 481 | VYEDLLAAGV ADPVKVTRSA LQNAASIAGL FLTTEAVVAD KPEKEKASVP GGGDMGGMDF |

In this specification the amino acid residues are designated by means of the following letters:

| | | | | | |
|---|---|---|---|---|---|
| A | alanine | I | isoleucine | R | arginine |
| C | cystine | K | lysine | S | serine |
| D | aspartic acid | L | leucine | T | threonine |
| E | glutamic acid | M | methionine | V | valine |
| F | phenyl alanine | N | asparagine | W | tryptophane |
| G | glycine | P | proline | Y | tyrosine |
| H | histidine | Q | glutamine | | |

It is further stated in European patent application 0 262 710 that antigen A cross-reacts serologically with antigens present in other bacterial species. This shows that epitopes present on antigen A are similarly present on equivalent proteins of various bacterial species, such as Mycobacterium, Escherichia, Treponema, Shigella, Salmonella, Yersinia, Nocardia, Campylobacter and Klebsiella. For example, it has been shown that the amino acid sequence of antigen A shows a very strong homology with the amino acid sequence of a protein from *Mycobacterium leprae* which is disclosed in Proc. Natl. Acad. Sci. USA 83, pages 7013-7017 (1986). For example, the amino acid sequence 134-205 of antigen A is identically present in the abovementioned 65 kD protein of *M. leprae*.

Further, European patent application 0 262 710 shows that antigen A itself is not arthritogenic, but can protect rats against arthritis induced by *M. tuberculosis*.

Finally, European patent application 0 262 710 describes the use of the T-cell clones A2b and A2c disclosed in EP-A-0 181 364 for the identification of antigens associated with arthritogenicity or with suppression of arthritogenicity. Both clones respond to whole mycobacteria, as well as to antigen A. For further localization of the epitope which is responsible for the stimulating activity of antigen A on the T-cell clones fragments of antigen A were investigated. These fragments were truncated derivatives produced by deletion mutants of the gene, and further fusion proteins with β-galactosidase, and synthetically prepared peptides. This investigation showed that the epitope responsible for the stimulation of the T-cell clones resides in antigen A amino acid sequence 171-240. European patent application 0 262 710 relates, among others, to polypeptides showing sequential homology with the polypeptide having antigen A amino acid sequence 171-240, which homology is such that the polypeptides are composed of 4-70 amino acid residues, and that in the amino acid sequence at least 4 amino acid residues are in the same relative position as the same amino acid residues are in the polypeptide having antigen A amino acid sequence 171-240. One of the polypeptides recognized by the T-cell clones A2b and A2c had antigen A amino acid sequence 180-196.

DESCRIPTION OF THE INVENTION

Further research resulted in a still more precise definition of the antigen A epitope recognized by T-cell clones A2b and A2c. Polypeptides were prepared by means of known solid phase techniques and these polypeptides were tested for their stimulating activity on the T-cell clones. The results are shown in the figure. The concentration of the peptides in the stimulation test was always 1 μg/ml. The proliferative reactions were measured by cultivating the T-cells (2×10⁴ per well) during 4 days in the presence of irradiated (1500 R) syngeneic thymocytes (2×10⁶ per well) as auxiliary cells, and then reacting the cells with ³H-thymidine during 16 hours. The number of counts per minute (cpm) for the thymidine uptake was measured in triplicate and was divided by the mean result of control tests without antigen carried out in triplicate. The mean values of the ratios so found are given as stimulation index (SI±standard deviation) SI=cpm test divided by cpm control without antigen. The culture medium was Dulbecco's Modified Eagles Medium (Gibco) supplemented with 1% rat serum, 5×10⁻⁵M 2-mercapto-ethanol, 2 mM glutamine, 100 units/ml penicilline and 100 μg/ml Streptomycine. In the same way heat-killed *M. tuberculosis* bacteria (H37Ra, Difco) were tested (Mt).

As the figure shows, the polypeptides having sequences 153-171, 185-196, 190-200 and 197-218 do not react, and the peptide having sequence 183-196 shows a slight reaction. The polypeptides having sequences 174-192, 180-196 and 180-188 are reactive.

It may be derived from these data that the epitope recognized by T-cell clones A2b and A2c resides in antigen A sequence 172-192, with sequence 180-188 as the most essential part.

It is interesting to notice that the amino acid sequence of a proteoglycan protein of cartilage (published in J. Biol. Chem. 261, pages 3519-3535 (1986)) which proteoglycan protein is also recognized by T-cell clones A2b and A2c, shows homology with antigen A sequence 180-188. A still stronger homology is shown by the sequence of an antigen from Epstein-Barr virus (Nature 310, pages 207-211 (1984)) which virus has been suggested to be related to the initiation of rheumatoid arthritis (J. Clin. Invest. 65, pages 1238-1242 (1980)). T-cell clone A2b responds to the polypeptide having this homologous sequence. Further, the sequence of HLA-DQ3 (J. Immunol. 139, pages 3506-3511 (1987)), which leucocyte antigen is mainly present in arthritis patients. (The Lancet ii, pages 1118-1120 (1987)) also shows homology with antigen A sequence 180-188. Finally, the amino acid sequence of human lamin A and C (Nature 319, pages 463-468 (1986) and PNAS 83, pages 6450-6454 (1986)) shows homology with antigen A sequence 180-188. Lamin A and lamin C are parts of the nuclear envelope of human cells, and are related to intermediate filament proteins. The T-cell clones react positively to this homologous structure. These homologies may be illustrated as follows:

```
180         188
```

| | |
|---|---|
| TFGLQLELT | Antigen A and *M. leprae* 65 kD |
| TAVVA<u>LELQ</u> | cartilage proteoglycan protein |
| TFG<u>LQ</u>PQDT | Epstein-Barr-virus antigen |
| RHNY<u>QLELR</u> | HLA-DQ3 |
| RARL<u>QLELS</u> | Lamin A and C |

The invention relates to the polypeptide having antigen A amino acid sequence 172-192 having the formula

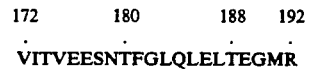

as well as to polypeptides derived therefrom, in the amino acid sequence of which sequence 172-179 and/or sequence 189-192 is (are) entirely or partially absent.

When sequence 172-179 and/or sequence 189-192 is (are) partially absent the parts of sequences 172-179 and 189-192 which are present in the polypeptide have the same amino acid sequence as in the above-mentioned formula of the polypeptide having antigen A sequence 172-192.

Also, the invention relates to polypeptides showing sequential homology with the above defined polypeptides. In this specification, polypeptides showing sequential homology are considered to be polypeptides composed of 9-21 amino acid residues, at least 4 of which are in the same relative position as in the polypeptide having antigen A amino acid sequence 172-192 or in the polypeptides derived therefrom and having a shorter sequence, as defined above.

More particularly, the invention relates to the polypeptide having antigen A sequence 180-188 and to the polypeptides showing sequential homology therewith, for example to the abovementioned polypeptides having sequences TAVVVALELQ, TFGLQPQDT, RHNYQLELR and RARLQLELS.

Although the T-cell clones A2b and A2c respond to all of the above defined polypeptides, the antigenicity and the immunogenicity of the polypeptides may be enhanced by coupling thereto at least one radical capable of improving the presentation of the antigenic determinants of the polypeptides. Suchs radicals are known in the art, and comprise, for example, radicals of peptides, tetanus toxoid, diphtheria toxoid, β-galactosidase and microbial outer membrane proteins. Multimers of the polypeptides in question are also contemplated. These modified polypeptides also form part of the invention.

All of the polypeptides according to the invention, viz. the polypeptide having antigen A amino acid sequence 172-192, the polypeptides derived therefrom and having an amino acid sequence in which sequence 172-179 and/or sequence 189-192 is (are) entirely or partially absent, the polypeptides showing sequential homology with said polypeptides, as well as the above defined modified peptides including the multimers, may be used as immunogens in pharmaceutical compositions, especially vaccines for the alleviation and the treatment of auto-immune diseases, especially arthritic conditions, and also as antigens in diagnostic compositions for the diagnosis of these diseases. These pharmaceutical and diagnostic compositions which may be prepared in a way known in the art, also form part of the invention. The activity of the above-defined modified peptides according to the invention is illustrated by the following experiments.

Protection against induction of adjuvant arthritis (AA) with *Mycobacterium tuberculosis* (Mt) was tested in rats. The immunogen was antigen A amino acid sequence 177-188 coupled to bovine serum albumin (BSA) by means of the well-known glutaraldehyde technique. Groups of five rats were given intraperitoneally BSA alone, 100 μg of the 177-188-BSA conjugate and 500 μg of the conjugate, respectively, in incomplete Freund's adjuvant. The BSA was given in a dose equivalent to the BSA content of 500 μg of 177-188-BSA. Seven days later, AA was induced in the rats by intracutaneous immunization with 1 mg of Mt suspended in 0.1 ml of mineral oil. Arthritis scores were determined by daily inspection of the joints with confirmation by histological examination at the end of the experiment. The results are shown in the following Table 1.

TABLE 1

Pre-immunization at day-7 with 177-188 conjugated to BSA protects against AA

| | Mean arthritic score (n = 5) after preimmunization with | | |
|---|---|---|---|
| | | 177-188 BSA | |
| Day | BSA alone | 100/μg | 500/μg |
| 11 | 0 | 0 | 0 |
| 15 | 4.0 | 1.5 | 0 |
| 19 | 7.0 | 2.3 | 1.0 |
| 25 | 2.3 | 2.8 | 1.1 |
| 32 | 1.7 | 1.8 | 0.8 |

The effect of immunization with the same 177-188 BSA conjugate was also tested at day 7 after Mt immunization. Also in this situation the arthritis that developed was less severe as compared to the arthritis seen in the BSA immunized control rats. The mean arthritis scores at the time of maximal arthritis (day 20) was 1 in the group of rats immunized with 100 μg and 1.8 in the group immunized with 500 μg, whereas the BSA immunized controls had a score of 6. (Each group existed of 6 animals).

The following experiment illustrates the immunogenic activity of the unmodified polypeptides of the invention.

In this experiment, arthritis was induced at day 0 in groups of 6 rats by intracutaneous administration of 1 mg of Mt suspended in 0.1 ml of mineral oil. At day 7 one group of rats received PBS alone, a second group received 10 μg of the peptide having antigen A amino acid sequence 180-188 solubilized in PBS, and a third group 100 μg of the peptide in PBS, all via the intravenous route.

Table 2 shows that the peptide significantly suppresses the development of arthritic symptoms.

TABLE 2

Immunization i.v. at day +7 with 180-188 in PBS protects against AA.

| | Mean arthritis score (n = 5) after immunization with | | |
|---|---|---|---|
| | | 180-188 in PBS i.v. | |
| Day | PBS alone | 10/ug | 100/ug |
| 14 | 5.0 | 2.0 | 1.2 |
| 16 | 6.4 | 3.8 | 2.8 |
| 20 | 10.7 | 7.4 | 4.4 |
| 22 | 12.8 | 3.8 | 2.0 |
| 24 | 9.4 | 4.2 | 2.4 |
| 27 | 6.4 | 3.2 | 1.8 |

The following experiments illustrate the use of the peptides according to the invention as antigens in immunological tests.

Sera from 36 juvenile rheumatoid arthritis (JRA) patients were tested in a standard solid phase RIA at a dilution of 1:40 and 1:80. For comparison, sera from 15 non-JRA arthritis patients, and control sear from 36 children with other diseases were tested. The JRA patients included 10 with poly-RA, 14 with pauci-RA and 12 with systemic RA.

Antigens were
1. AP, the acetone precipitable fraction of *Mycobacterium tuberculosis* according to EP-A 0 181 364;
2. Antigen A;
3. Peptide having antigen A amino acid sequence 180-188;
4. Peptide having amino acid sequence TAVVALELQ occuring in cartilage proteoglycan protein.

The tests were carried out as follows:
Antigens were coated upon microtitre plates by adding to each well 2.5 μg of antigen in 50 μg of PBS. After incubation for two hours at room temperature the wells were washed with PBS, and blocked with 1% BSA/PBS. After 30 minutes incubation at room temperature the wells were washed 3 times with PBS and sera were added in dilutions 1:40 and 1:80 in 1% BSA/PBS. After incubation for two hours at room temperature, and washing 3 times with PBS, 100,000 counts per minute of radioactive iodine labeled goat-anti-human immunoglobulin were added to each well. After incubation overnight at 40° C. and washing 4 times with PBS the radioactivity was measured. Reaction was deemed positive when it was at least twice the standard deviation above mean of controls. The results are given in the following Table 3.

TABLE 3

| Antigen | Sera giving positive reaction with antigens (%) | | |
|---|---|---|---|
| | JRA | Non-JRA | Controls |
| AP | 72 | 13* | 0 |
| Antigen A | 72 | 13* | 0 |
| Antigen A 180-188 peptide | 88 | 0 | 0 |
| TAVVALELQ | 80 | 13* | 0 |

*The two positives among the 15 NON-JRA patients (13%) had arthritis of the knees and erythrema nodosum.

Another way to improve the immunogenicity of the polypeptides according to the invention is to construct, by known genetical engineering methods, micro-organisms expressing a polypeptide according to the invention either as such or as part of a fusion protein or as a multimer thereof. These micro-organisms can be used for the preparation of a live vaccine which will provoke not only the production of antibodies and the development of cellular immunity against the microorganism in question, but will also be useful for the alleviation and treatment of auto-immune diseases.

These genetically engineered micro-organisms and pharmaceutical compositions containing these, also form part of the invention. Examples of suitable genetically engineered micro-organisms are Vaccinia, *Mycobacterium bovis* BCG and Salmonella strains.

Finally, the invention provides kits for performing immunological tests comprising a container with at least one of the antigenic compounds discussed above, or a container with the diagnostic composition mentioned above.

The antigenic compounds and diagnostic compositions, as well as the diagnostic kits according to the invention may be used for various types of assays, such as:

a.1. a lymphocyte proliferation test, or determination of any entity indicative of such proliferation;
a.2. indicative of the measure of lymphocyte activation are also changes which can be assayed by standard means so as to establish the presence and degree of lymphocyte activation: amongst these there may be mentioned:
  a. production of lymphokines (such as interleukin-2 (IL-2);
  b. gamma interferon;
  c. migration inhibition factor (MIF);
  d. expression of membrane markers, such as IL-2 receptor; peanut agglutination receptor;
  e. expression of enzymes such as heparanase.
b. determination of antibody titer in absolute terms or as a ratio of the values obtained by different compositions, said values or ratios being indicative of the presence or absence of the disease. Quantitative values obtained are of use in establishing the severity of the disease.

The diagnostic compositions according to the invention may be prepared by combining one or more antigenic compounds according to the invention as above defined with suitable adjuvants and auxiliary components. Standardized kits with reference and calibration means are of value in the rapid and convenient determination of arthritic disease and its stage and/or severity.

FIGURE

| Peptide | Sequence 171  181  191<br>GVITVEESNTFGLQLELTEGMRFDKGYISG | T-cell reaction SI (± 1 SD) | |
|---|---|---|---|
| | | A2b | A2c |
| 153-171 | ⊢⊣ | <1 | =1 |
| 174-192 | ⊢————⊣ | 16 (± 2) | 11 (± 2) |
| 180-196 | ⊢—————⊣ | 33 (± 5) | 120 (± 8) |
| 180-188 | ⊢——⊣ | 47 (± 4) | 58 (± 3) |
| 183-196 | ⊢————⊣ | 9,2 (± 3) | 2,9 (± 8) |
| 185-196 | ⊢———⊣ | <1 | <1 |
| 190-200 | ⊢———⊣ | <1 | <1 |
| 197-218 | ⊢→ | <1 | <1 |
| Mt | | 180 (± 21) | 304 (± 18) |

We claim:
1. A peptide made up of from 9 to 21 amino acid residues including in its amino acid sequence a sequence selected from among TFGLQLELT, TAVVALELQ, TFGLQPQDT, RHNYQLELR and RARLQLELS.
2. Polypeptide according to claim 1 having the amino acid sequence TFGLQLELT.

3. Polypeptide according to claim 1 having the amino acid sequence TFGLQLELT TAVVALELQ, TFGLQPQDT, RHNYQLELR or RARLQLELS.

4. A multimer of peptides made up of from 9 to 21 amino acid residues including in its amino acid sequence a sequence selected from among TFGLQLELT, TAVVALELQ, TFGLQPQDT, RHNYQLELR and RARLQLELS.

5. A multimer according to claim 4, wherein the peptides have an amino acid sequence selected from among TFGLQLELT, TAVVALELQ, TFGLQPQDT, RHNYQLELR and RARLQLELS.

6. A composition comprising a peptide made up of from 9 to 21 amino acid residues including in its amino acid sequence a sequence selected from among TFGLQLELT, TAVVALELQ, TFGLQPQDT, RHNYQLELR and RARLQLELS coupled to at least one radical enhancing its antigenicity and immunogenicity.

7. Compounds according to claim 6 in which the radical enhancing the immunogenicity is a radical of a peptide, of tetanus toxoid, of diphtheria toxoid, of β-galactosidase, or of a microbial outer membrane protein.

8. A pharmaceutical composition comprising a peptide made up of from 9 to 21 amino acid residues including in its amino acid sequence a sequence selected from among TFGLQLELT, TAVVALELQ, TFGLQPQDT, RHNYQLELR and RARLQLELS and a pharmaceutically acceptable carrier.

9. A composition according to claim 8, wherein the peptide includes the amino acid sequence TFGLQLELT.

10. A composition according to claim 8, wherein the peptide includes the amino acid sequence TAVVALELQ.

11. A composition according to claim 8, wherein the peptide includes the amino acid sequence TFGLQPQDT.

12. A composition according to claim 8, wherein the peptide includes the amino acid sequence RHNYQLELR.

13. A composition according to claim 8, wherein the peptide includes the amino acid sequence RARLQLELS.

* * * * *